United States Patent [19]

Bischof, deceased et al.

[11] Patent Number: 4,915,688

[45] Date of Patent: Apr. 10, 1990

[54] APPARATUS FOR ADMINISTERING SOLUTION TO A PATIENT

[75] Inventors: Reinhard Bischof, deceased, late of Baldham; by Ursula Bischof, heiress, Gelsenkirchen, both of Fed. Rep. of Germany

[73] Assignee: Baxter International Inc., Deerfield, Ill.

[21] Appl. No.: 128,655

[22] Filed: Dec. 3, 1987

[51] Int. Cl.4 ............................................ A61M 37/00
[52] U.S. Cl. ........................................ 604/83; 137/606
[58] Field of Search .................. 128/762, 764, 766; 604/191, 410, 88, 89, 258, 284, 80–86, 246, 247; 141/105, 244, 245, 236, 237; 222/145; 137/606

[56] References Cited

U.S. PATENT DOCUMENTS

| | | | |
|---|---|---|---|
| 2,866,457 | 12/1958 | Moore | 137/606 |
| 2,999,499 | 9/1961 | Willet | 604/83 |
| 3,557,778 | 1/1971 | Hughes | 604/191 |
| 3,941,126 | 3/1976 | Dietrich et al. | 604/83 |
| 4,084,606 | 4/1978 | Mittleman | 137/102 |
| 4,433,974 | 2/1984 | Bishoff | 604/407 |
| 4,535,819 | 8/1985 | Atkinson et al. | 604/247 |

FOREIGN PATENT DOCUMENTS

| | | | |
|---|---|---|---|
| 737249 | 6/1966 | Canada | 604/191 |
| 2630050 | 1/1978 | Fed. Rep. of Germany . | |
| 7814016 | 9/1978 | Fed. Rep. of Germany . | |
| 7610486 | 11/1976 | France . | |
| 8400340 | 2/1984 | PCT Int'l Appl. . | |
| 2020554 | 11/1979 | United Kingdom . | |
| 2059776 | 4/1981 | United Kingdom | 604/81 |

OTHER PUBLICATIONS

Letter Attachment, Quest Medical Inc. Carrollton, Tex. 75006 Nov., 1982.
Two catalog pages from Quest Medical Inc., 3312 Wiley Post Rd., Carrollton, Tex. 75006.

Primary Examiner—Jerome L. Kruter
Attorney, Agent, or Firm—Paul C. Flattery; Amy L. H. Rockwell; Mary J. Schnurr

[57] ABSTRACT

An apparatus for producing and/or administering medicines and nutritional solutions to a patient. The apparatus includes a multiway valve having a plurality of inlets, an outlet and a collecting reservoir between the inlets and the outlet. The multiway valve may also have an injection site and connection that can be used both as an inlet and an outlet. The inlets, outlets and injection site each include a one-way valve which allows flow only in the direction from the inlets to the patient. A syringe may be connected to the inlet/outlet connection to draw an amount of solution form one or more of the solution bags and then move the solutions together into a mixing bag connected at the outlet, to prepare a medicine or nutritional solution.

14 Claims, 2 Drawing Sheets

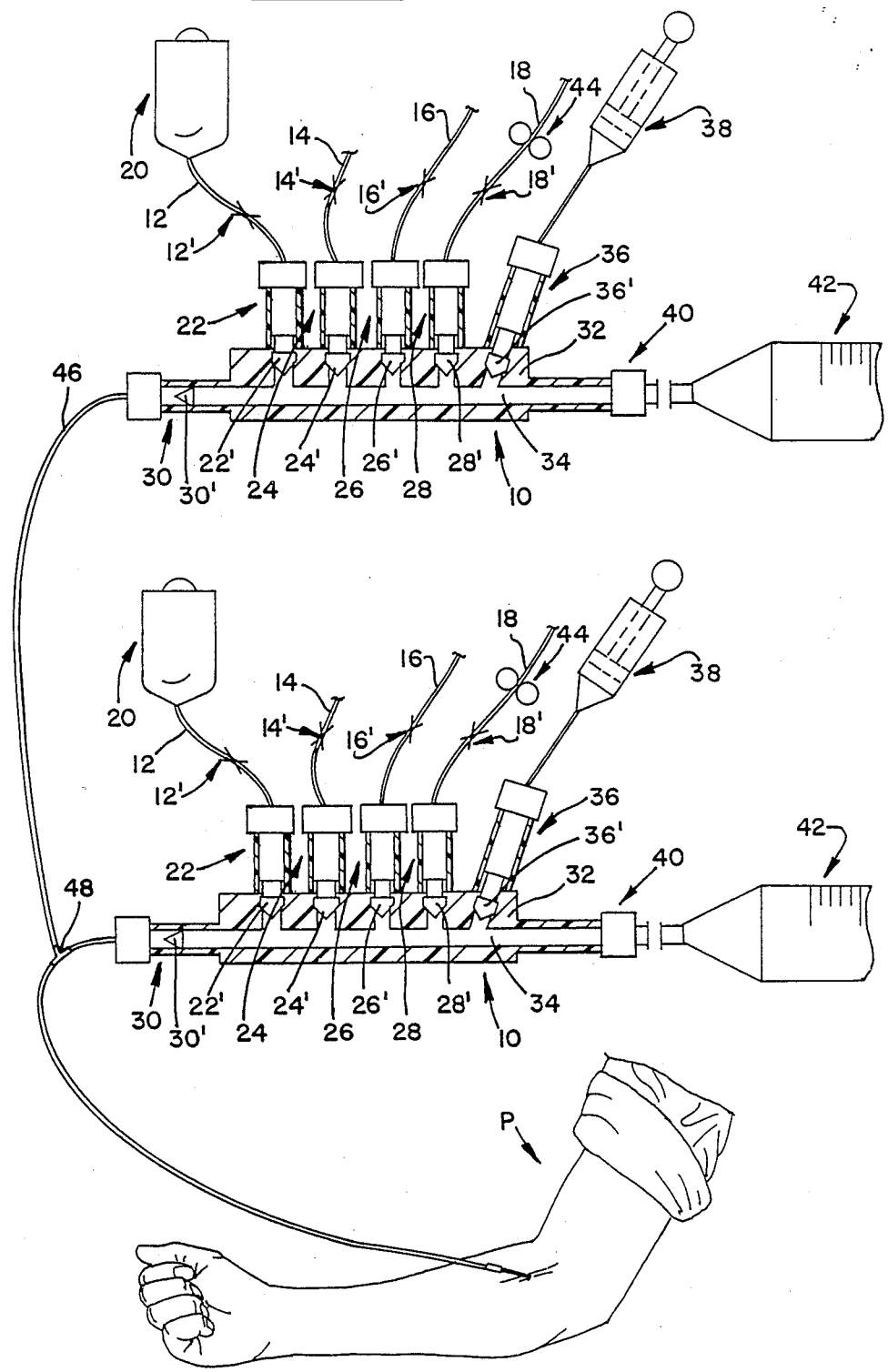
FIG_2

APPARATUS FOR ADMINISTERING SOLUTION TO A PATIENT

FIELD OF THE INVENTION

This invention relates to a valve for the administration and/or production of medicines and nutrient solutions, and in particular parenteral nutrient solutions.

DESCRIPTION OF RELATED ART

Arrangements for producing a parenteral nutrient solution are known in the art. One such arrangement is shown in U.S. Pat. No. 4,433,974. However, that document leaves the construction of the multiway valve largely undefined. In any case the known multiway valve has only a single inlet to which the individual block tube connections may connect the supply containers. In that design, the tube connections are joined prior to being connected to the inlet of the multiway valve.

One problem of this known arrangement is that the number of supply containers which may be connected is relatively restricted. Furthermore, the known arrangement cannot be used for administering infusions, since there is the danger of uncontrolled mixing of the various solutions from the supply containers prior to the solutions entering the single valve inlet. Above all there is the danger of osmotic mixing in the individual tube connections because of the differing consistency and specific weights of the individual solutions.

In the known arrangement this problem plays only a small role, since the solutions are drawn individually and are administered into a mixing bag, and the solutions are not directly administered to a patient. The undesired and uncontrolled mixing of solutions in the tube connections can be prevented in the known arrangement only by manually blocking the tube connections near the inlet.

The same problem occurs with two other known embodiments for administering infusions. The first of these embodiments consists of a continuous line into which the individual inlet connections are made. In the area adjacent each connection there is positioned a three-way stopcock.

The second embodiment comprises a continuous line into which the individual inlet connections are made. A manually operable block stopcock is connected to each individual inlet. A stopcock is also positioned at the end connections of the continuous line.

In both embodiments, it is necessary to manually actuate a plurality of three-way stopcocks or blocking stopcocks, to avoid the undesired and uncontrolled mixing of solutions in the tube connections. It is obvious that this manual handling involves the risk of incorrect stopcock settings, which can lead to serious complications, even fatal results, during surgical procedures. The known arrangements also lack separate injection sites &or injecting a predetermined dose of a drug. The known systems are also relatively complicated and space-consuming and it is correspondingly difficult for an operator to ensure the correct functional switching of those systems.

The present invention provides a solution to the problems discussed above and is particularly well suited for administering infusions without the risk of inadvertant mixing of the various infusion solutions in the area of the tube connections and the supply containers. Moreover, the invention is suited to simultaneously preparing precise solutions of& total parenteral nutrition or TPN.

Further, it is an object of the invention to make the handling of the arrangement functionally safe and "foolproof", so that incorrect settings and therefore wrong infusions are avoided. Finally, the multiway valve is sterilizable simply and surely by means of gas.

SUMMARY OF THE INVENTION

In improving the known arrangements, a seemingly more complicated valve was devised, but with the result that different infusion solutions can be safely administered. These infusion solutions may include a parenteral multi-nutrient solution, an electrolyte, bicarbonate, gamma globulin, fat, blood lidocain (for heart stabilization), etc.

An infusion pump is preferably coupled to several tube connections. For example, an infusion pump might be connected to the tube connection leading to the supply container for lidocain and bicarbonate, to enable an operator to administer more or less lidocain and/or bicarbonate to the patient should complications arise during surgery. Bicarbonate is used, for example, when acidosis occurs. Lidocain is used for heart stabilization.

Individual solutions can also be administered by attaching a syringe-type device to the connection of the multiway valve that serves both as an inlet and an outlet, by drawing solutions from the supply containers and then by administering this solution through the outlet of the multiway valve. An uncontrolled back mixing of the drawn-in solutions will not occur because of the nonreturn valves positioned at each individual inlet.

By using the connection acting both as inlet and outlet it is possible to prepare in the conventional manner parenteral nutrient solutions. A syringe at the inlet/outlet connection is simply used to draw in solutions and then expel them through the outlet of the multiway valve which is connected to a mixing container, such as a mixing bag.

The multiway valve used in the embodiment described herein does not have any mechanically actuable rotary stopcocks which cause sterilization problems. It is not practical to sterilize those stopcocks, since the sterilization gas does not reach the bearing or slide surfaces of the rotary stopcocks. It may be possible to gamma sterilize the stopcocks. However, the silicone film serving as lubricant and sealing film on the bearing and slide surfaces of the rotary stopcocks still presents a sterilization problem. None of these problems arise with the multiway valve according to the present invention.

Preferably the present invention includes an injection site which is also connected to the collecting reservoir of the multiway valve for the injection of prescribed amounts of a certain drug.

It is of particular importance that in the embodiment described herein the individual solutions will not mix together even if the unused tube connections are inadvertently not clamped off by tube clips or the like. In the instant invention, the tube connection must be blocked off only when the corresponding infusion solution is not to be administered or drawn up by suction.

If two or more tube connections are open in the known arrangement, and an infusion pump is connected to a tube connection, there is the danger that a part of the solution conveyed by the infusion pump may be transferred into the other open tube lines. This would result in the uncontrolled mixing of infusion solutions and administration of a correspondingly uncontrolled dosage to the patient. For this reason in the known systems it is necessary to block the tube connections and/or individual inlets individually and manually. If this is inadvertently neglected, the damage may be considerable, especially in the case of critical operations.

The multiway valve disclosed herein can be made extremely compact. The individual inlets can also be arranged in a row very close to one another. Further, it is also possible to distribute the individual inlets in a star pattern. However, actual practice has shown that the arrangement of the individual inlets in a series is advantageous in that it simplifies the entire system.

BRIEF DESCRIPTION OF THE DRAWINGS

FIG. 2 is a partial sectional schematic view of two of the arrangements for administering solution to a patient in accordance with the present invention, joined in parallel.

DESCRIPTION OF THE PREFERRED EMBODIMENT

Figure 1:
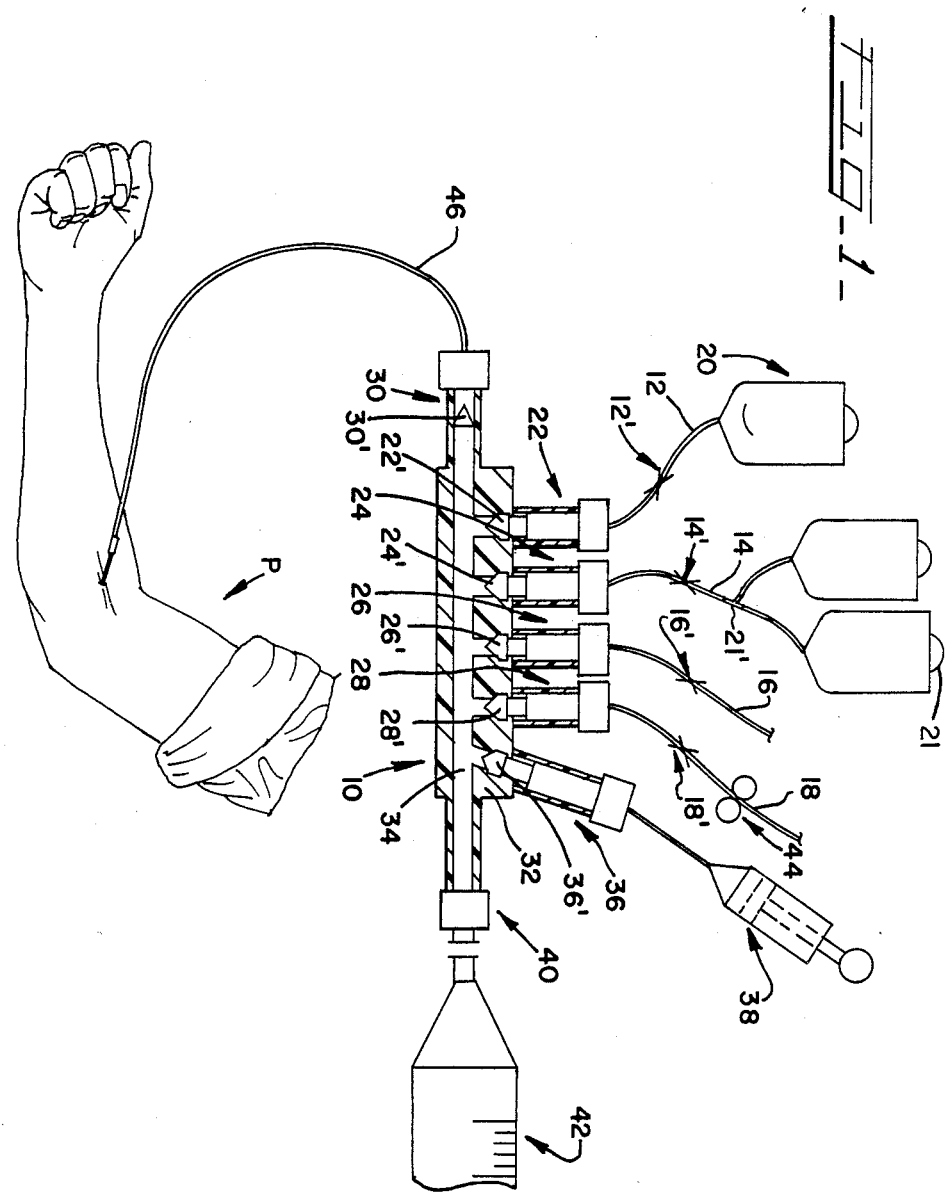
FIG. 1 a partial sectional schematic view of the arrangement for administering solution to a patient in accordance with the present invention.

Referring now to FIG. 1, an arrangement including a multiway valve constructed according to the invention is shown. FIG. 1 shows an arrangement for administering and/or producing medical drugs and/or nutritional solutions, especially parenteral nutritional solutions, using a multiway valve 10. The multi-way valve is shown connected to four supply containers, such as an electrolyte, bicarbonate, gamma-globulin and lidocain, over tube connections 12, 14, 16, 18. The tube connections 12, 14, 16, 18 may each be individually blocked or clamped off by means of tube clips 12', 14', 16' and 18', which are preferably roller clamps. One supply container is shown connected to tube 12. Alternatively, two supply containers 21 are shown connected to tube 14 at Y-site 21'. The multiway valve 10 has four separate inlets 22, 24, 26, 28, each including a nonreturn valve, 22', 24', 26' and 28', such as a beak valve connected to each tube. Although four inlets are shown in the present embodiment, any number may be used. The valves 22', 24', 26' and 28' open only in the direction from the inlet to an outlet 30. The outlet also has a nonreturn valve 30', such as a beak valve, which ooens only in the direction from the individual inlets 22, 24, 26, 28 to the outlet 30. Thus the infusion cannot back up from the patient P.

The individual inlets 22, 24, 26, 28 issue into a common collecting reservoir 34 which is a continuous channel inside the valve body 32.

Into this collecting reservoir or channel 34 there also issues a conventional injection site for injecting a prescribed amount of a drug by a syringe 38. The outlet 30 leading to the patient P and a connection 40 effective both as inlet and outlet are both connected to the collecting reservoir or channel 34. This connection 40 has no nonreturn valve. Connection 40 may be closed by a cap or a blocking stopcock (not shown). If necessary a suction device may also be connected to this connection. The suction device may be a suction syringe or perfusor syringe 42, which can be used to draw in partial amounts from the supply bags and to administer these amounts to the patient, preferably in a time-controlled manner. To prepare a parenteral nutrient solution the outlet 30 is connected with a mixing container, such as a mixing bag (not shown). The multiway valve described herein may thus be used for many applications.

Infusion pumps may be located at one or more tube connections 12, 14, 16, 18. In the embodiment described herein an infusion pump 44 (schematically represented) is allocated to the tube connection or line 18.

The individual inlets 22, 24, 26, 28 each have a Luer connection for coupling to the tube connections or lines 12, 14, 16, 18. Moreover, the individual inlets 22, 24, 26, 28 are constructed as flexible connecting members, so that they may be positioned close to one another. The inlets can be slightly bent away from one another, in order to facilitate manipulations in connecting the tube connections 12, 14, 16, 18. Theoretically, the individual inlets 22, 24, 26, 28 may be distributed over the circumference of the collecting space or passage channel 34. However, practice has shown that the arrangement of the individual inlets 22, 24, 26, 28 in a series one after the other provides the best control of the system. The outlet 30, as well as the inlet/outlet connection 40 each use a Luer coupling. It is significant that the arrangement taught herein is a closed system to substantially reduce the danger of contamination.

The nonreturn valves 22', 24', 26', 28', 30' are solidly connected inside each respective valve body. A nonreturn valve 36' is also positioned inside the valve body 32 adjacent the injection connection piece 36. Nonreturn valve 36' is openable only in the direction from the injection site to the outlet 30. The patient line 46 leads from the outlet 30 to the patient P.

By means of the syringe 42 a special infusion mixture can be prepared even during an operation, and then quickly administered to the patient. This feature is especially useful when complications arise during surgery.

The multiway valve according to the instant invention can be constructed to be extremely compact. The number of individual inlets that may be constructed is essentially unlimited, although presently the maximum number necessary is eight. To avoid the difficulties encountered when the multiway valves are too large, two or more multiway valves of the type described herein can be joined parallel to one another as seen in FIG. 2. The outlets can be joined at a Y-site 48 before the connection to the patient feed line 46.

Using the present invention even without clamping the tube connections 12, 14, 16, 18, one infusion solution will not force its way into another tube connection or line. This is automatically prevented by the nonreturn valves 22', 24', 26', 28'.

In summary, the arrangement according to the instant invention utilizing the multiway valve described herein provides a simple, functionally safe, contamination-free system that is suitable both for administering infusions and also for producing medicines or nutrient solutions to be administered.

While the invention has particularly been shown and described with reference to a preferred embodiment, it will be understood by those skilled in the art that variations in form, construction and arrangement may be made therein without departing from the spirit and scope of the invention. All such variations are intended to be covered in the appended claims.

I claim:

1. Apparatus for administering medicinal or nutritional solutions, comprising:
    a multiway valve having a one-piece valve body, said valve body having a plurality of inlets, a collecting reservoir, and an outlet; each of said inlets allowing flow only from the inlet to said collecting reservoir; said outlet being connectable to a patient, said outlet having a non-return valve allowing flow only from said collecting reservoir to outside said valve;

2. Apparatus as claimed in claim 1 wherein said multiway valve additionally comprises an additional connection which may be used as either an inlet or an outlet, said connection further being adapted for connection to a suction device.

3. Apparatus as claimed in claim 2 wherein the connection may be blocked from communication with said inlets and said outlet.

4. Apparatus as claimed in claim 2 wherein said additional connection being adapted to be closed by a blockable stopcock.

5. Apparatus as claimed in claim 4 wherein each of said inlets comprises a Luer coupling which is connected to a flexible tubular connecting piece with the valve body.

6. Apparatus as claimed in claim 4 wherein two containers are connected to each of said inlets, wherein the tubes leading from two complementary containers are joined together prior to joining the respective inlet.

7. Apparatus as claimed in claim 2, additionally comprising an infusion pump connected to one of said tubes.

8. Apparatus as claimed in claim 1 wherein one of said tubes may be blocked from the respective container by a tube clip.

9. Apparatus as claimed in claim 1 wherein said multiway valve additionally comprises an injection site, said injection site including a nonreturn valve allowing flow only from injection site toward said outlet.

10. Apparatus as claimed as claimed in claim 1 additionally comprising:
   a second multiway valve having a plurality of inlets, a collecting reservoir, and an outlet, each of said inlets allowing flow only from the inlet to said collecting reservoir, said outlet being connectable to a patient, said outlet allowing flow only from said collecting resevoir to outside said valv;
   a second set of supply containers containing medicinal or nutritional solution;
   a second set of individually blockable tubes, each of said tubes being connected between one of said second set of supply containers and one of said inlets of said second multiway valve; and
   a connector joining the outlet of said first multiway valve and the outlet of said second multiway valve prior to said outlets being connected to the patient.

11. Apparatus for administering medicinal or nutritional solutions, comprising:
   a multiway valve having a plurality of inlets, a collecting reservoir, an outlet, an injection site, and an additional connection; each of said inlets allowing flow only from the inlet to said collecting reservoir, said outlet being connectable to a patient, said outlet having a non-return valve allowing flow only from said collecting reservoir to downstream of said valve, said injection site including a non-return valve allowing flow only from said injection site toward said outlet; said additional connection may be used as an inlet, an outlet or blocked, said additional connection further being adapted for connection to a suction device;
   a plurality of supply containers containing medicinal or nutritional solution; and
   a plurality of individually blockable tubes, each of said tubes being connected between one of said supply containers and one of said inlets.

12. Apparatus as claimed in claim 11 wherein each of said inlets comprises a Luer coupling which is connected to a flexible tubular connecting piece with the valve body.

13. Apparatus as claimed in claim 11 wherein two containers are connected to each of said inlets, wherein the tubes leading from two complimentary containers are joined together prior to joining the respective inlet.

14. Apparatus as claimed in claim 11, additionally comprising an infusion pump connected to one of said tubes.

* * * * *

UNITED STATES PATENT AND TRADEMARK OFFICE
CERTIFICATE OF CORRECTION

PATENT NO. : 4,915,688

DATED : 4-10-90

INVENTOR(S) : Reinhard Bischof, deceased

It is certified that error appears in the above-identified patent and that said Letters Patent is hereby corrected as shown below:

In the abstract, line 6 which reads "an injection site and connection that..." should read "an injection site and a connection that..."; line 11 which reads "amount of solution form one or..." should read "amount of solution from one or...";

in column 1, line 57 which reads "&or injecting a..." should read "for injecting a..."; line 68 which reads "solutions of& total parenteral..." should read "solutions of total parenteral...";

in column 3, line 14 which reads "Fig. 1 a partial sectional..." should read "FIG. 1 is a partial sectional"; line 16 ends in a period and should end in a semi-colon; and, line 45 which reads "...which ooens only in the..." should read "...which opens only in the...";

in column 5, line 41 which reads "...outside said valv;" should read "...outside said valve;".

UNITED STATES PATENT AND TRADEMARK OFFICE
CERTIFICATE OF CORRECTION

PATENT NO. : 4,915,688

DATED : 4-10-90

INVENTOR(S) : Reinhard Bischof, deceased

It is certified that error appears in the above-identified patent and that said Letters Patent is hereby corrected as shown below:

1. Apparatus for administering medicinal or nutritional solutions, comprising:

a multiway valve having a one-piece valve body, said valve body having a plurality of inlets, a collecting reservoir, and an outlet; each of said inlets allowing flow only from the inlet to said collecting reservoir; said outlet being connectable to a patient, said outlet having a non-return valve allowing flow only from said collecting reservoir to outside said valve;

a plurality of supply containers containing medicinal or nutritional solution; and a plurality of individually blockable tubes, each of said tubes being connected between one of said supply containers and one of said inlets.

Signed and Sealed this

First Day of September, 1992

Attest:

DOUGLAS B. COMER

*Attesting Officer*     *Acting Commissioner of Patents and Trademarks*